United States Patent
Tang et al.

(10) Patent No.: US 11,168,143 B2
(45) Date of Patent: Nov. 9, 2021

(54) AFUCOSYLATED MONOCLONAL ANTIBODY

(71) Applicants: BEIJING GEFUCURE BIOTECHNOLOGY LIMITED COMPANY, Beijing (CN); Wuxi Kingenew Biotechnology Limited Company, Jiangsu (CN)

(72) Inventors: Bo Tang, Beijing (CN); Ran Zhang, Beijing (CN); Jianmin Zhao, Jiangsu (CN); Jianwu Wang, Jiangsu (CN); Yunping Dai, Beijing (CN)

(73) Assignees: Beijing Gefucure Biotechnology Limited Company; Wuxi Kingenew Biotechnology Limited Company

( * ) Notice: Subject to any disclaimer, the term of this patent is extended or adjusted under 35 U.S.C. 154(b) by 60 days.

(21) Appl. No.: 16/345,648

(22) PCT Filed: Jul. 24, 2017

(86) PCT No.: PCT/CN2017/094095
§ 371 (c)(1),
(2) Date: Apr. 26, 2019

(87) PCT Pub. No.: WO2018/076828
PCT Pub. Date: May 3, 2018

(65) Prior Publication Data
US 2020/0270358 A1 Aug. 27, 2020

(30) Foreign Application Priority Data
Oct. 26, 2016 (CN) .......................... 201610947520.2

(51) Int. Cl.
*C07K 16/28* (2006.01)
*A61P 35/00* (2006.01)
*A61K 39/00* (2006.01)

(52) U.S. Cl.
CPC .......... *C07K 16/2887* (2013.01); *A61P 35/00* (2018.01); *A61K 2039/505* (2013.01); *C07K 2317/40* (2013.01); *C07K 2317/732* (2013.01); *C07K 2317/92* (2013.01)

(58) Field of Classification Search
CPC ............ C07K 16/2887; C07K 2317/40; C07K 2317/732; C07K 2317/92; C07K 2317/94; C07K 2317/12; C07K 16/04; C07K 2317/14; C07K 2317/41; C07K 2317/24; A61P 35/00; A61P 35/02; A61K 2039/505; C12N 15/8509
See application file for complete search history.

(56) References Cited

U.S. PATENT DOCUMENTS

| 7,319,139 B2 | 1/2008 | Braslawsky | |
| 2009/0060921 A1* | 3/2009 | Dickey | C12N 15/8258 424/152.1 |
| 2013/0149300 A1* | 6/2013 | Hiatt | C07K 16/32 424/133.1 |
| 2014/0046033 A1 | 2/2014 | Schindler et al. | |
| 2014/0140988 A1 | 5/2014 | Eldering et al. | |

FOREIGN PATENT DOCUMENTS

| CN | 1989154 A | 6/2007 |
| CN | 101484470 A | 7/2009 |
| CN | 101588817 A | 11/2009 |
| CN | 103261229 A | 8/2013 |
| CN | 103524621 A * | 1/2014 |
| CN | 104204217 A | 12/2014 |

OTHER PUBLICATIONS

Zhang et al., J of Animal Science, suppl 4, vol. 94: 180 (Year: 2016).*
Kurogochi et al., PLOS One 10(7): e0132848 (Year: 2015).*
Lloyd et al., Protein Engineering, Design & Selection 22:159-168 (Year: 2009).*
Edwards et al., J Mol Biol. 334(1): 103-118 (Year: 2003).*
Yu et al., Investigative Ophthalmology & Visual Science 49(2): 522-527 (Year: 2008).*
Witte et al., Cancer and Metastasis Reviews 17: 155-161 (Year: 1998).*
Stancovski et al., Proceedings of the National Academy of Science USA 88: 8691-8695 (Year: 1991).*
Cochran et al., J. Immunol. Meth. 287: 147-158 (Year: 2004).*
International Search Report for Application No. PCT/CN2017/094095 dated Oct. 16, 2017.

* cited by examiner

*Primary Examiner* — Phuong Huynh
(74) *Attorney, Agent, or Firm* — Mendelsohn Dunleavy, P.C.

(57) ABSTRACT

Provided is an afucosylated monoclonal antibody. The monoclonal antibody is a human IgG antibody and has an afucosylated sugar chain structure at a heavy-chain sugar chain binding site. Also provided are application of the monoclonal antibody in the preparation of antineoplastic drugs, and a composition containing the monoclonal antibody. Compared with a fucosylated monoclonal antibody, the provided afucosylated monoclonal antibody has higher biological activity in vitro and in vivo and can be used for developing more effective therapeutic monoclonal antibody drugs.

5 Claims, 2 Drawing Sheets
Specification includes a Sequence Listing.

AFUCOSYLATED MONOCLONAL ANTIBODY

TECHNICAL FIELD

The present invention belongs to the field of genetic engineering, and specifically relates to an afucosylated monoclonal antibody.

BACKGROUND ART

Protein glycosylation is one of the most common post-translational modifications. It is a process of transferring oligosaccharides to proteins under the action of glycosyltransferases to form glycosidic bonds with specific amino acid residues on proteins. The types of glycosylation of proteins in mammals are mainly divided into three classes: a N-linked sugar chain composed of one or more monosaccharide units, an O-linked sugar chain, and a GPI glycosylphosphatidylinositol anchor. Glycosylation modification allows different proteins to have different labels, and a single glycosylation site can produce significant heterogeneity due to differences in the mass number of glycoproteins and the number of charges. The oligosaccharide chain structures of glycoproteins are diverse, have abundant identifying information, and thus involve many biological regulation and recognition processes, including receptor recognition, inflammation and autoimmune diseases, signal transduction and metabolism and the like. In addition, the characteristics such as safety, efficacy, and serum half-life of therapeutic proteins are also affected by glycosylation patterns thereof.

As the most important class of therapeutic proteins, the effectiveness of recombinant monoclonal antibody drugs is also highly dependent on correct glycosylation patterns thereof. All monoclonal antibodies currently approved for treatment are immunoglobulin G (IgG), and mostly IgG1. Studies show that the CH2 region of the human IgG heavy chain Fc segment contains a conserved N-linked glycosylation site of Asn-297. Thus, each IgG can have two N-linked di-branched or multi-branched complex-type biantennary oligosaccharides, including more than 30 different types of sugar chains, and thus the antibody can exhibit a high degree of heterogeneity. Analysis of the sugar chain pattern indicates that the N-sugar chain structure at Asn-297 site of human IgG is usually a core-fucosylated di-branched complex-type core structure with up to two galactose (Gal) residues as the terminal. The core structure includes two β-N-acetylglucosamine (GlcNac) and three mannose (Man) units. According to the number and binding mode of the terminal Gal residues, the glycoforms of the antibody can be divided into various types such as G0, G1 and G2, and some have core-fucosylation, such as G0F, G1F and the like. The Fc segment of an antibody is a ligand-binding site of cytotoxic effector cells, and thus the presence of a sugar chain structure is critical for antibody-mediated effector functions such as antibody-dependent cell-mediated cytotoxicity (ADCC).

Currently, 43% of antibody drugs approved by the United States and the European Union are produced by CHO cells, 50% are derived from other mouse-derived engineering cells (NSO or SP2/0), and only 7% are non-glycosylated antibodies expressed by E. coli. Although early experiments demonstrated that CHO could produce antibodies the glycoform of which is consistent with that of human serum antibody, the glycosylation of antibodies produced by most engineered cell lines is still different from that of human serum antibodies. For example, glycoforms of antibodies produced by mouse-derived animal cells rarely have bisecting galactoside modification, the proportion of fucose modification is high, and the degree of galactoside (G) modification is also lower than that of human serum antibodies. Thus, the main type of glycoforms of antibodies produced by mouse-derived animal cells is G0F, but the type of human serum antibody glycosylation is mainly G1F. For example, anti-human CD20 chimeric monoclonal antibody-rituximab (trade name, Rituxan) developed by Roche Company for treatment of B-cell lymphoma, is produced by expression using mammalian cell lines, and the sugar chain structure thereof is mainly the core structure fucosylated G0F glycoform. In recent years, many studies show that removal or reduction of fucose groups can significantly enhance the ADCC activity of therapeutic antibodies, which thereby show higher efficacy in vivo and in vitro.

SUMMARY OF THE INVENTION

One purpose of the present invention is to overcome the above-mentioned defects of the existing monoclonal antibodies and to provide an afucosylated monoclonal antibody having high biological activity in vitro.

In order to achieve the above purpose, the present invention provides an afucosylated monoclonal antibody. The monoclonal antibody is a human IgG antibody, and the glycoform core structure of the monoclonal antibody is mainly afucosylated glycoform.

Preferably, the afucosylated glycoform of the glycoform core structure of the monoclonal antibody accounts for 80% to 100%.

Preferably, the G2 glycoform of the glycoform core structure of the monoclonal antibody accounts for 30% to 100% of the afucosylated glycoform.

Preferably, the G2 glycoform monoclonal antibody means that the glycoform core structure of the antibody does not contain a fucose group, and the terminal of the sugar chain has two galactose groups.

Preferably, the glycoform core structure of the G2 glycoform monoclonal antibody is a sugar chain structure represented by the following formula (I):

formula (I)

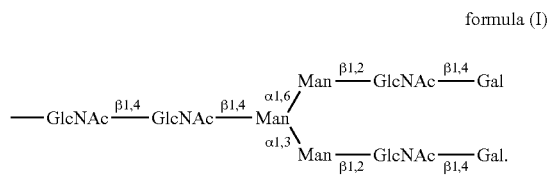

Preferably, the monoclonal antibody is an anti-CD20 antibody.

Preferably, the amino acid sequence of the heavy chain of the monoclonal antibody is represented by SEQ ID NO. 1.

Preferably, the amino acid sequence of the light chain of the monoclonal antibody is represented by SEQ ID No. 2.

The present invention provides the use of the above monoclonal antibody in the preparation of a drug.

The drug is used for treating a CD20-expressing cancer.

The drug is used for treating or diagnosing B-cell lymphoma.

A drug containing the monoclonal antibody of the present invention is also within the protection scope of the present invention.

The present invention also provides a composition for treating cancer, wherein, the composition contains any one of the above-mentioned monoclonal antibodies.

The present invention also provides a method of producing the above monoclonal antibody, wherein a transgenic animal is used for production via mammary gland expression.

Preferably, the transgenic animal is a transgenic cow.

Compared with a fucosylated monoclonal antibody, the afucosylated monoclonal antibody provided by the present invention has higher biological activity in vitro and in vivo and can be used for developing more effective therapeutic monoclonal antibody drugs

SPECIFIC MODES FOR CARRYING OUT THE EMBODIMENTS

The present invention will be described in detail below in combination with specific embodiments.

The following examples are intended to illustrate the present invention, but are not intended to limit the scope of the present invention. Unless otherwise specified, the technical means used in the examples are conventional means well known to a person skilled in the art, and the materials used are all commercially available. For molecular cloning methods, see *Molecular Cloning Laboratory Cloning* (3$^{rd}$ Edition, Science Press). For cell manipulation methods, see *Culture of Animal Cells—A Manual of Basic Technique and Specialized Applications Guide* (6$^{th}$ Edition, Science Press).

EXAMPLE 1: STRUCTURE OF AFUCOSYLATED ANTI-CD20 ANTIBODY

The present invention provides an afucosylated human IgG monoclonal antibody, the glycoform core structure of which is mainly afucosylated glycoform, accounting for 50% to 100%, wherein the G2 glycoform accounts for 30% to 100% of the afucosylated glycoform, and the glycoform core structure of the G2 glycoform antibody does not contain a fucose group, and the terminal of the sugar chain has two galactose groups.

Figure 1:
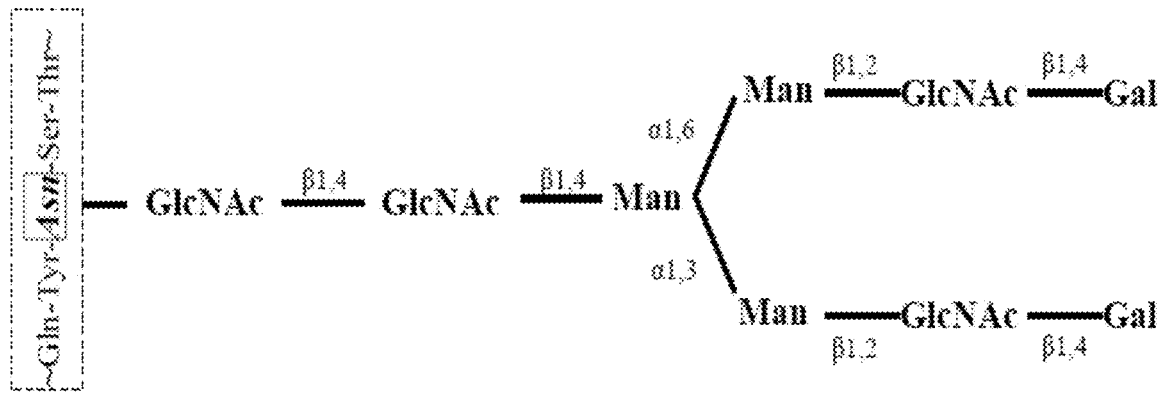
FIG. 1 shows the glycoform structure of the anti-CD20 antibody, wherein, GlcNAc: N-acetylglucosamine; Man: mannose; Gal: galactose.

The afucosylated monoclonal antibody provided by the present invention may be any human IgG monoclonal antibody, wherein an afucosylated anti-CD20 antibody is preferred, the heavy-chain amino acid sequence thereof is represented by SEQ ID No. 1, and the light-chain amino acid sequence thereof is represented by SEQ ID No. 2, wherein the sugar chain structure of the Asn-320 site on the heavy chain is as shown in FIG. 1. Compared with the main glycoform of Rituxan monoclonal antibody (the content of fucosylated glycoforms such as G0F, G1F and G2F in the glycoform structure of Rituxan anti-human CD20 antibody is greater than 95%, while the proportion of afucosylated glycoforms such as G0 glycoform and the like is less than 5%), the glycoform core structure of the anti-CD20 monoclonal antibody provided by the present invention is mainly afucosylated glycoform, wherein the proportion of the afucosylated glycoform accounts for 50% to 100%, wherein the G2 glycoform accounts for 30% to 100% of the afucosylated glycoform, while the glycoform core structure of the antibody of the G2 glycoform does not contain a fucose group, and the terminal of the sugar chain has two galactose groups.

EXAMPLE 2: EXPRESSION AND ACQUISITION OF AFUCOSYLATED ANTI-CD20 ANTIBODY

The heavy-chain gene sequence and the light-chain gene sequence of the anti-human CD20 antibody were designed using the amino acid sequences SEQ ID No. 1 and SEQ ID No. 2 as described in Example 1, respectively, and a commercial mammary gland-specific expression vector such as pBC1 vector can be used. The mammary gland-specific expression vector can also be designed according to relevant literatures. The structure for expressing the recombinant monoclonal antibody mainly includes the upstream regulatory region of genes for mammary gland-specific expression, the gene sequence for the heavy-chain or the gene sequence for the light-chain, and the downstream regulatory region of the genes for mammary gland-specific expression. The afucosylated anti-CD20 antibody provided by the present invention is produced by mammary gland expression of transgenic animals selected from transgenic cows, transgenic sheep, transgenic rabbits, transgenic pigs and transgenic cattle.

Taking the transgenic cow as an example, the above-mentioned heavy-chain gene mammary gland expression vector and the light-chain gene mammary gland expression vector for the monoclonal antibody were mixed at a molar ratio of 1:1, the mixed solution was transfected into the cow fibroblast or oviduct epithelial cells by electroporation or microinjection, and after transfection, single-cell cloning culture and amplification were carried out. Primers were designed using the sequence of the transfected vector, and transgenic cells into which the heavy chain gene and the light chain gene are integrated simultaneously were obtained by PCR molecular detection. The transgenic cells were used as nuclear donors for nuclear transplantation, and the nuclear of the transgenic cell was transplanted into the cow oocyte which had been previously denucleated with a micromanipulator, and a transgenic embryo in which the heavy chain gene and the light chain gene were co-integrated was obtained. The non-surgical embryo transplantation technique widely used in breeding production of cows was adopted to transplant the transgenic embryo into the body of a surrogate cow, so as to obtain a transgenic cow in which the heavy chain gene and the light chain gene were co-integrated after expiration of pregnancy. After the transgenic cow was sexually mature, the artificial insemination technique widely used in breeding production of cows was adopted to perform breeding for the transgenic cow, and after pregnancy, the transgenic cow gave birth to calves. The artificial insemination technique was also used in the subsequent production of transgenic cows. The recombinant monoclonal antibody was purified from the milk produced by the transgenic cows, i.e., the recombinant monoclonal antibody with a purity of more than 95% was obtained by separation using Protein A of GE Company (see product specification for the operation method). After identification by amino acid sequencing, it was confirmed that the heavy-chain amino acid sequence and the light-chain amino acid sequence of the recombinant monoclonal antibody were identical to SEQ ID No. 1 and SEQ ID No. 2, respectively, indicating that the recombinant monoclonal antibody produced by the transgenic cow was a recombinant anti-human CD20 antibody.

EXAMPLE 3: IDENTIFICATION OF THE GLYCOFORM OF THE RECOMBINANT AFUCOSYLATED ANTI-CD20 ANTIBODY

The types and contents of oligosaccharide chains between the recombinant antibody prepared in Example 2 and Rituxan were compared by LC-MS. PNGase F was added to the above sample of intact recombinant antibody, mixed well, incubated at 37° C. for 24 hours. Cold ethanol was added to a final concentration of 75%, the obtained mixture was placed in ice bath for 20 minutes, then the resultant was subject to HILIC and freeze-drying. 50 µl of 2-AB labeling solution was added to the freeze-dried carbohydrates, shook to make the carbohydrates completely dissolved, incubated at 65° C. for 5 hours in the dark, and the resultant was subjected to HILIC, freeze-drying, re-dissolving, and loading. The molecular weight was accurately determined by first-stage mass spectrometry so as to determine the type of free oligosaccharide. The content of main glycoforms was calculated by the area normalization method.

After analysis, the glycoform structure of the recombinant anti-human CD20 antibody expressed by the transgenic cow has a fucosylated glycoform content of less than 0 to 15%, while the afucosylated glycoform monoclonal antibody accounts for 80% to 100%, and the G2 glycoform (the glycoform core structure does not have fucose group, and the terminal of the sugar chain has two galactose groups) monoclonal antibody accounts for 30% to 100% of the afucosylated glycoform. As a control, Rituxan is mainly of fucosylated glycoform such as G0F, G1F and G2F, accounting for more than 95%, and the afucosylated glycoform accounts for less than 5%.

EXAMPLE 4: ADCC EXPERIMENT OF AFUCOSYLATED ANTI ANTI-CD20 ANTIBODY

Daudi and Raji cells (purchased from the Cell Center of Institute of Basic Medical Sciences, Peking Union Medical College) were selected as target cells. Daudi and Raji cells were both B lymphoma cells cultured in vitro, and the two cells both contain CD20 antigen molecules on surface thereof, and are widely used for the detection of cellular activity of anti-CD20 antibodies. The recombinant monoclonal antibody (experimental group), commercially available Rituxan (positive control group) and physiological saline (negative control group) were used.

Figure 2:
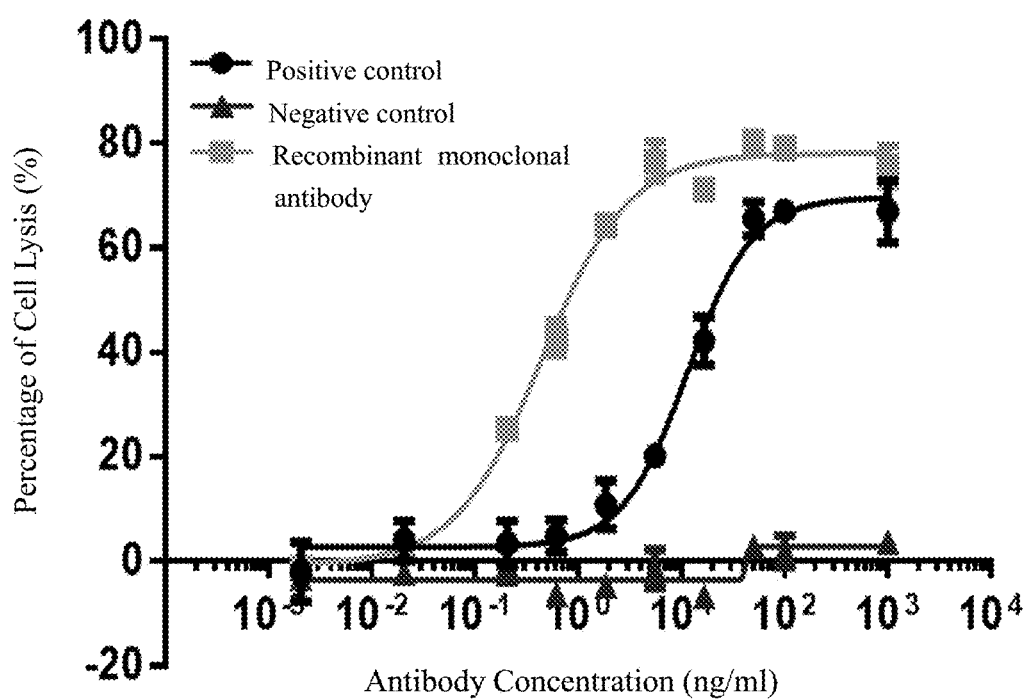
FIG. 2 shows results of antibody-dependent cell-mediated cytotoxicity (ADCC) assay of the recombinant antibody according to Example 3 of the present invention, wherein anti-CD20 is a recombinant antibody; Rituxan is commercial rituximab as a positive control; and Herceptin is a negative control.

The target cells were collected by centrifugation, followed by resuspending and washing with Assay buffer, then centrifuging and discarding the supernatant for use. The target cell density was adjusted to 4× concentration, i.e., $2\times10^5$/mL, using ADCC buffer, followed by plating into a 96-well plate at 50 µL per well, adding antibody and co-incubating with the target cells for 30 minutes. Effector cells NK/92/CD16a (158 v/v) were added to the incubated experimental well plates for continue incubating for 6 hours. After the incubation was finished, all the cells were precipitated to the bottom of the plate by centrifugation at a low speed, 50 µL of the supernatant was pipetted into a new 96-well plate, 50 µL of a LDH test solution was added, then incubation was performed at room temperature for 30 minutes. The OD value of the LDH reaction was detected on Flexstation 3, with a detection wavelength of OD492 nm and a background wavelength of $OD_{650}$ nm. The dose-effect curve was analyzed using Sigmoidal dose-response (variable slope) of GraphPad Prism version 6.0. As shown in FIG. 2, the recombinant anti-CD20 monoclonal antibody prepared in Example 2 and Rituxan monoclonal antibody both induce a sample concentration-dependent ADCC effect (antibody-dependent cell-mediated cytotoxicity) on target cells, and the negative control Herceptin cannot induce an effective ADCC effect on Daudi. The ADCC effect of the recombinant monoclonal antibody is higher than that of Rituxan, which is consistent with the previous glycosylation prediction result.

EXAMPLE 5: PHARMACODYNAMIC EXPERIMENTS OF THE RECOMBINANT ANTIBODY IN MICE

Figure 3:
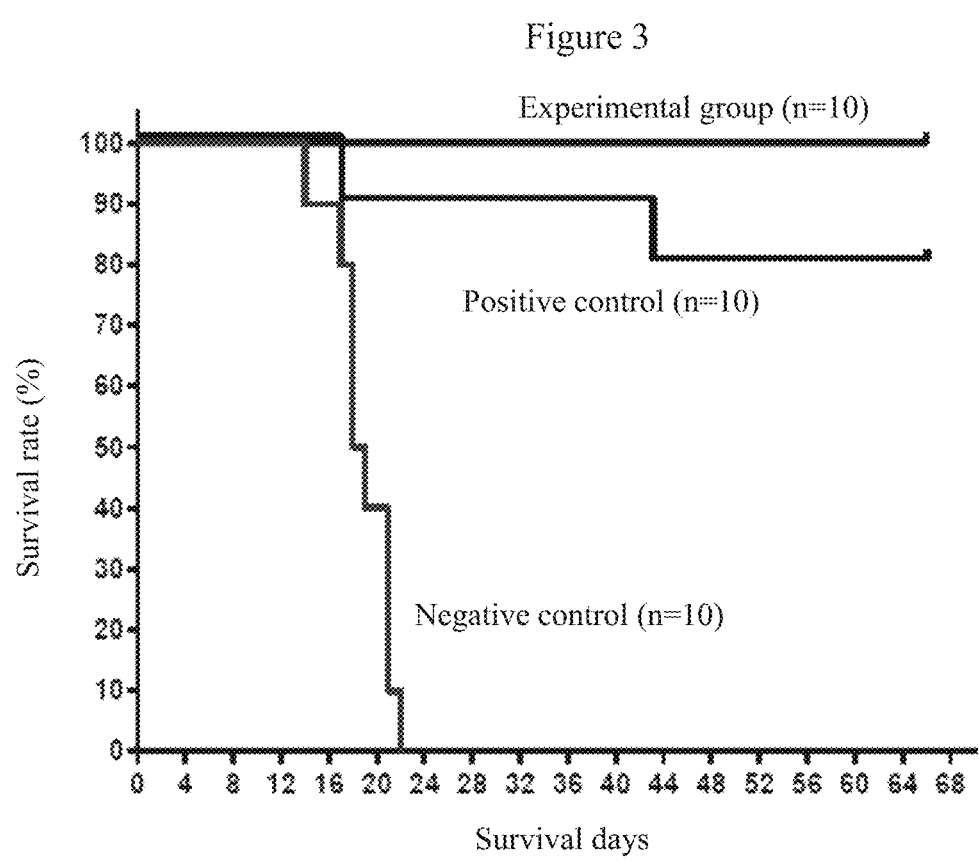
FIG. 3 shows results of pharmacodynamic experiments in mice according to Example 4 of the present invention, wherein the experimental group is a recombinant antibody; the positive control is commercial Rituxan; and the negative control is physiological saline.

Raji cells were amplified and injected into the caudal vein of 30 SCID mice at $4\times10^6$ cells/mouse to establish a model. The mice were randomly divided into 3 groups of 10 mice each, and the administration of drugs was started immediately. The drugs included the recombinant monoclonal antibody prepared in Example 2 (experimental group), the commercially available Rituxan (positive control group) and physiological saline (negative control group). The injection dose was 100 µg/mouse. The survival situation of the mice was monitored. The experiment ended 66 days after administration to each group. As shown in FIG. 3, the mice in the physiological saline negative control group were respectively euthanized on the 14th, 17th, 18th, 19th, 21st, and 22nd day after administration due to hind limb paralysis. Two mice in the Rituxan positive control group were found to be hind limb paralyzed and euthanized respectively on the 17th day and 43th day after administration. No mice in the antibody test group was found to be paralyzed or euthanized, and the antibody shows a good effect on the Raji lymphoma systemic model. In-vivo pharmacodynamic experiments of the recombinant antibody in mice indicate that the afucosylated anti-CD20 antibody prepared in Example 2 of the present invention can be used for the treatment of CD20-expressing cancers, including B cell lymphoma and the like.

EXAMPLE 6: DETERMINATION OF THE AFFINITY BETWEEN THE RECOMBINANT ANTIBODY AND HUMAN FC RECEPTOR

The affinity between two Fc receptors (human CD16a (158 Phe) and human CD16a (158 Val)) (purchased from Beijing Baipu Saisi Biological Technology Co., Ltd.) and the recombinant antibody prepared in Example 2 were detected by Surface Plasmon Resonance (SPR). A channel with immobilized Fc receptor proteins (human CD16a (158 Phe) and human CD16a (158 Val)) was used as a detection channel, and a channel without immobilized Fc receptor protein was used as a control channel The specific process was as follows: (1) surface equilibration: the surface of the chip was equilibrated with HBS-EP buffer at a flow rate of 10 µl/min for 5 min; (2) surface activation: a 'NHS+EDC' 1:1 mixed solution was injected to activate the surface of the chip at a flow rate of 10 µl/min for 7 min; (3) protein coupling: Fc receptor protein (diluted in 10 mM sodium acetate (pH 5.0) buffer) was injected for coupling at a flow rate of 10 µl/min for about 7 min; with respect to the control channel, this step was omitted; and (4) surface blocking: ethanolamine was injected to block the surface at a flow rate of 10 µl/min for 7 min. The detection temperature of the affinity analysis experiment was 25° C., and the buffer system was HBS-EP. A multi-cycle assay was used in the experiment, and each cycle was divided into two steps of: injecting a series of concentrations of analytes to the chip surface to monitor binding and dissociation signals, and chip regeneration. Results were shown in Table 1. The results show that the affinities between the recombinant anti-CD20 antibody prepared in Example 2 of the present invention and the two Fc receptors are both higher than that between Rituxan and corresponding receptors.

TABLE 1

Results of affinity between recombinant antibody and human Fc receptor

| | 158Val/Phe | $K_a$ (1/Ms) | $K_d$ (1/s) | $K_D$ (M) |
|---|---|---|---|---|
| Rituxan | Val | $4.6 \times 10^4$ | $4.3 \times 10^{-2}$ | $9.4 \pm 0.02 \times 10^{-7}$ |
| Recombinant monoclonal antibody | Val | $1.7 \times 10^5$ | $1.0 \times 10^{-2}$ | $5.9 \pm 0.01 \times 10^{-8}$ |
| Rituxan | Phe | $2.5 \times 10^4$ | $1.7 \times 10^{-1}$ | $6.8 \pm 0.02 \times 10^{-6}$ |
| Recombinant monoclonal antibody | Phe | $2.1 \times 10^5$ | $2.7 \times 10^{-2}$ | $1.3 \pm 0.02 \times 10^{-7}$ |

INDUSTRIAL APPLICABILITY

The present invention provides an afucosylated monoclonal antibody. The monoclonal antibody is a human IgG antibody and has an afucosylated sugar chain structure at a sugar chain binding site of the heavy-chain. The present invention also provides application of the monoclonal antibody in the preparation of antineoplastic drugs, and a composition containing the monoclonal antibody. Compared with a fucosylated monoclonal antibody, the afucosylation monoclonal antibody provided by the present invention has higher biological activity in vitro and in vivo and can be used for developing more effective therapeutic monoclonal antibody drugs.

INCORPORATION OF SEQUENCE LISTING BY REFERENCE

The sequence listing in the enclosed ASCII text file named "CNHK1026US_Amended_Seq_List.txt," created on May 2, 2020 with a size of 15 Kilobytes is hereby incorporated-by-reference.

What is claimed is:

1. An afucosylated monoclonal antibody, wherein
the afucosylated monoclonal antibody is a human IgG anti-CD20 antibody, and the glycoform core structure of the afucosylated monoclonal antibody is mainly afucosylated glycoform;
the afucosylated glycoform accounts for 80% to 100% of the glycoform core structure of the monoclonal antibody;
the glycoform has a G2 glycoform core structure that accounts for 30% to 100% of the afucosylated glycoform;
the G2 glycoform means that the glycoform core structure of the antibody does not contain a fucose group, and the terminal of the sugar chain has two galactose groups;
the glycoform core structure of the G2 glycoform monoclonal antibody is a sugar chain structure represented by the following formula (I):

formula (I)

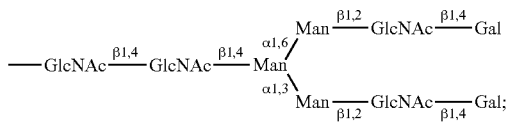

and
the antibody comprises a heavy chain and a light chain, wherein the heavy chain comprises the amino acid sequence of SEQ ID NO: 1, and the light chain comprises the amino acid sequence of SEQ ID NO: 2.

2. A drug comprising the afucosylated monoclonal antibody according to claim 1.

3. A composition for treating CD20-expressing cancer, wherein the composition comprises the afucosylated monoclonal antibody according to claim 1.

4. The afucosylated monoclonal antibody according to claim 1, wherein the antibody is produced by mammary gland expression of a transgenic cow.

5. A method of producing the afucosylated monoclonal antibody of claim 1, comprising transforming a host cell with a mammary gland expression vector comprising a nucleic acid sequence encoding the heavy chain amino acid sequence of SSEQ ID NO:1 and the light chain amino acid sequence of SEQ ID NO:2, and
purifying the antibody from milk of a transgeinc cow.

* * * * *

SEQUENCE LISTING

```
<160> NUMBER OF SEQ ID NOS: 2

<210> SEQ ID NO 1
<211> LENGTH: 470
<212> TYPE: PRT
<213> ORGANISM: Artificial sequence
<220> FEATURE:
<223> OTHER INFORMATION: Chimeric sequence containing Mouse and Human
      sequences

<400> SEQUENCE: 1

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

```
Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 2
<211> LENGTH: 235
<212> TYPE: PRT
<213> ORGANISM: Artificial sequence
<220> FEATURE:
<223> OTHER INFORMATION: Chimeric sequence containing Mouse and Human
      sequences

<400> SEQUENCE: 2

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Ile His Trp Phe Gln Gln Lys Pro Gly Ser Ser
        50                  55                  60

Pro Lys Pro Trp Ile Tyr Ala Thr Ser Asn Leu Ala Ser Gly Val Pro
```

```
65                  70                  75                  80
Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Thr Ser Asn Pro Pro Thr Phe Gly Gly Thr Lys Leu Glu Ile Lys
                115                 120                 125

Arg Thr Val Ala Ala Pro Ser Val Phe Ile Phe Pro Pro Ser Asp Glu
                130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```